United States Patent [19]

Colapicchioni et al.

[11] Patent Number: 5,160,597
[45] Date of Patent: Nov. 3, 1992

[54] SENSOR WITH ANTIGEN CHEMICALLY BONDED TO A SEMICONDUCTOR DEVICE

[75] Inventors: Claudio Colapicchioni; Filippo Porcelli; Carlo A. Nuzzolo, all of Rome, Italy

[73] Assignee: Eniricerche S.p.A., Milan, Italy

[21] Appl. No.: 507,994

[22] Filed: Apr. 12, 1990

[30] Foreign Application Priority Data

Apr. 21, 1989 [IT] Italy ................. 20259 A/89

[51] Int. Cl.$^5$ ............................. G01N 27/26
[52] U.S. Cl. ................... 204/403; 204/418
[58] Field of Search ............. 204/403, 418; 524/58; 435/817, 7.2, 4; 436/806, 518

[56] References Cited

U.S. PATENT DOCUMENTS

| 4,269,682 | 5/1981 | Yano et al. | 204/418 |
| 4,708,947 | 11/1987 | Maruyama et al. | 524/58 |
| 4,839,017 | 6/1989 | Taniguchi et al. | 204/403 |

FOREIGN PATENT DOCUMENTS

| 0127438 | 12/1984 | European Pat. Off. . |
| 0155193 | 9/1985 | European Pat. Off. . |
| 0291130 | 11/1988 | European Pat. Off. . |
| WO88/09808 | 12/1988 | PCT Int'l Appl. . |

OTHER PUBLICATIONS

Biological Abstracts, vol. 81, No. 9, 1986, p. AB-945, 86703, S. J. Huber, "Improved Solid-Phase Enzyme Immunoassay Systems in the Parts-per-Trillion Range for Atrazine in Fresh Water".

*Primary Examiner*—John Niebling
*Assistant Examiner*—Bruce F. Bell
*Attorney, Agent, or Firm*—Oblon, Spivak, McClelland, Maier & Neustadt

[57] ABSTRACT

A description is given, together with relative preparation processes, of a sensor containing an immunochemical membrane and a device of EOS or CHEMFET type containing surface silicon oxide adhering to said membrane via a polysiloxane matrix, characterized in that the immunochemical membrane is formed from a functionalized antigen or from the same functionalized antigen bonded to a protein, said immunochemical membrane being bonded chemically to the polysiloxane matrix by functional groups present on the same antigen or by bifunctional coupling agents.

2 Claims, 8 Drawing Sheets

SENSOR WITH ANTIGEN CHEMICALLY BONDED TO A SEMICONDUCTOR DEVICE

This invention relates to a semiconductor device of EOS (electrolyte oxide semiconductor) or CHEMFET (chemical field effect transistor) type containing a polysiloxane matrix and an immunochemical membrane formed from a monolayer consisting of an antigen or a polymeric multilayer consisting of an antigen and a protein.

In current clinical diagnostics, the hematic concentration of metabolytes, hormones or proteins is determined using various processes employing immunofluorescent (FIA etc.), immunoradiometric (RIA, IRMA etc.) or immunoenzymatic (ELISA etc.) systems.

Recently, the attention of various groups of researchers has turned towards the construction of immunosensors using as transducers solid state devices such as FETs which are able to detect a very small quantity of charge present on the active zone of the transducer, ie the gate. The advantages of this type of sensor compared with traditional processes are mainly the considerable miniaturization of the device, the low cost of the transducer and the rapidity of sensor response, in addition to the at least theoretically high sensitivity which should be attained (10 mV of signal for analyte concentrations of between $10^{-7}$ and $10^{-11}$M) [see "Annals N.Y. Acad of Sciences" 428, 286 (1984) by J. Janata and G. F. Blackburn].

Various prototypes have so far been constructed in which the antibody is adsorbed on the FET gate and the bond with the antigen to be determined produces an electrical charge variation which can be recorded by the transducer [see "J. Membr. Sc.", 2, 125 (1977) by M. Aizawa, S. Kato and S. Suzuki, and "Ion-sensitive Electrodes in Analytical Chemistry" (1980) (Freiser H. ed.), 2, 107-174, Plenum Press, by J. Janata and R. J. Huber].

However the resultant immunochemical membrane is rather unstable and in particular is subject to interference by other chemical species such as ions or proteins present in solution. It has been surprisingly found that by constructing an immunochemical membrane consisting of a functionalized antigen (and possibly a protein) chemically bonded to the surface silicon oxide of the device by a polysiloxane matrix, the membrane maintains its biological functionality constant for more than one month if stored in a pH 7.8 buffered solution.

In addition said interference problems can be overcome by marking the antibody directed against the antigen to be determined, or marking a second antibody directed against this antibody, with an enzyme such as glucose oxidase or urease, which during the catalyzed reaction produces electrical charges detected by the transducer (EOS or CHEMFET).

SUMMARY OF THE INVENTION

A first aspect of the present invention is a sensor containing an immunochemical membrane, and a device of EOS or CHEMFET type containing surface silicon oxide adhering to said immunochemical membrane by a polysiloxane matrix, characterised in that the immunochemical membrane is formed from a monolayer consisting of an antigen or a polymeric multilayer consisting of an antigen and a protein, said immunochemical membrane being bonded chemically to the polysiloxane matrix by functional groups present on the same antigen or by bifunctional coupling agents which bond the same protein, the polysiloxane matrix being chosen from functional organosilanes of general formula:

where $R^{II}$, $R^{III}$ and $R^{IV}$, which can be equal or different, are $C_1$–$C_{10}$ alkyl or alkoxy groups,

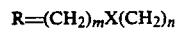

where X is $CH_2$ or a mono or polycondensed aromatic group or NH or O, m and n, which can be equal or different, are whole numbers between 0 and 10, but not 0 when X is NH or O, Y can be $-NH_2$ or $-OH$ or $-SH$, or from functional organosilanes of general formula:

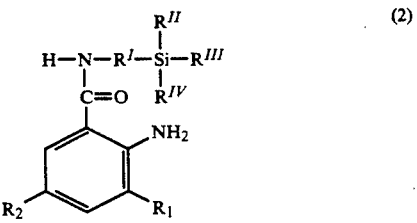

in which $R_1$ and $R_2$, which be equal or different, are Cl, Br, $CH_3$, $NO_2$, $NH_2$ or H, $R^{II}$, $R^{III}$ and $R^{IV}$, which can be equal or different, are $C_1$–$C_{10}$ alkyl or alkoxy groups, $R^I$ can be a $C_1$–$C_{10}$ alkyl, aminoalkyl, aminoalkylaryl or alkylaryl group.

For example aminoethylaminopropyltrimethoxysilane (AEAPS) or anthranylamidepropyltriethoxysilane (AAPS) can be used as the polysiloxane matrix.

Besides containing surface silicon oxide an EOS device must contain in the part below the silicon oxide a layer of aluminum or gold deposited by evaporation.

If a functional organosilane of formula (2) is used, its preparation process comprises reacting isatoic anhydride or its derivatives with aminosilanes of type

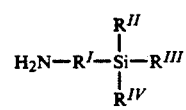

in accordance with the following scheme:

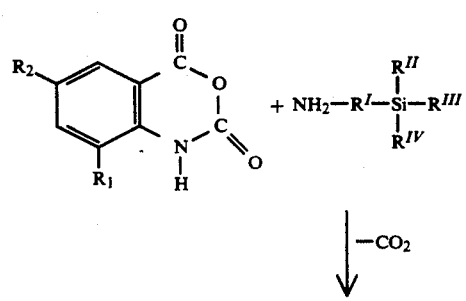

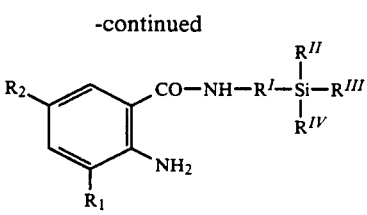

DETAILED DESCRIPTION OF THE PREFERRED EMBODIMENTS

Figure 1:
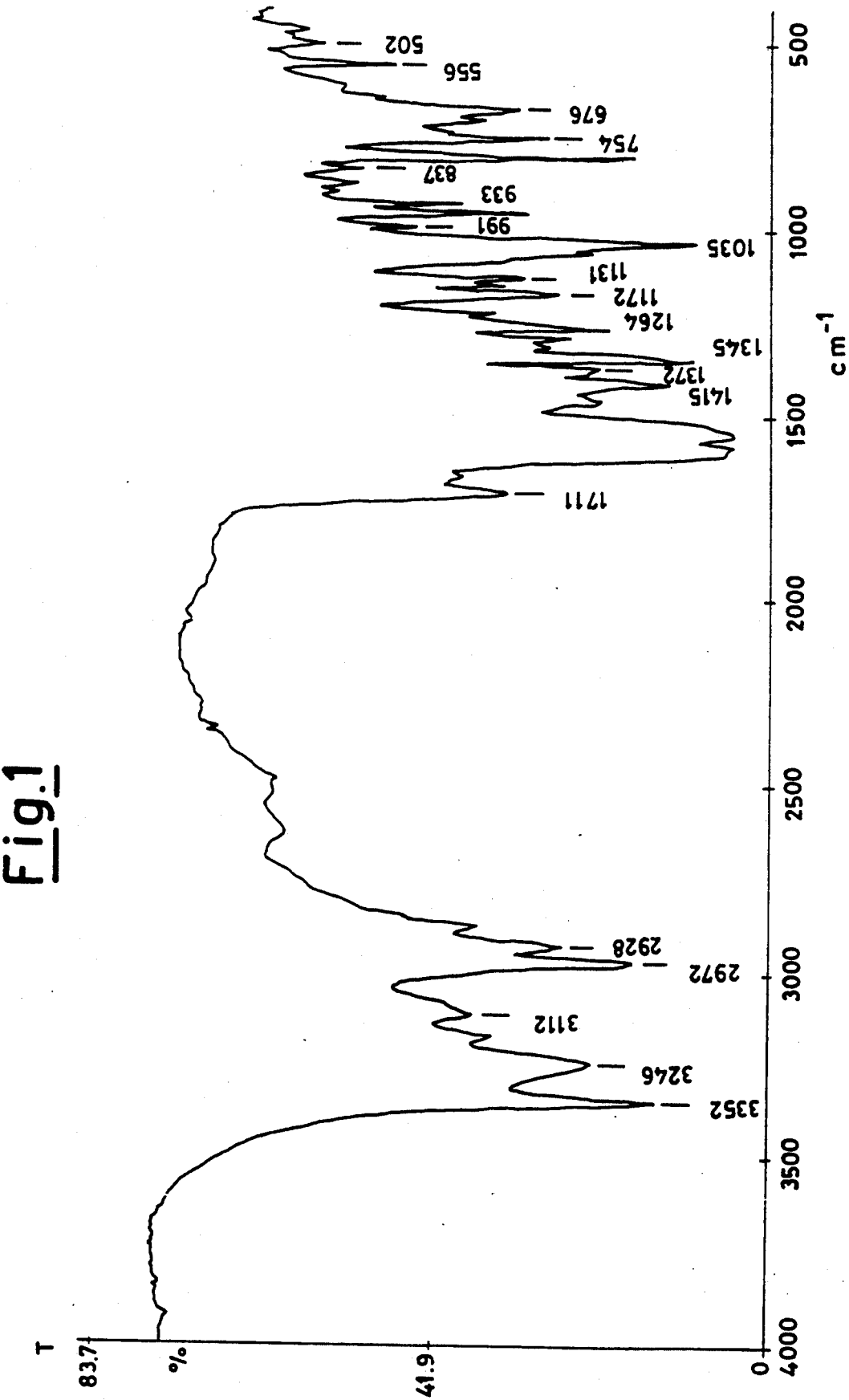
FIG. 1 is showing the formation of ametryne sulphoxide as monitored by ETIR.

The preferred silanes for preparing the functional organosilanes for the purposes of the present invention are:

3-aminopropyltriethoxysilane
$H_2N-(CH_2)_3-Si-(OC_2H_5)_3$
aminomethyltriethoxysilane
$H_2N-CH_2-Si-(OC_2H_5)_3$
2-aminoethyl-aminopropyltriethoxysilane
$H_2N-(CH_2)_2-NH-(CH_2)_3-Si-(OCH_3)_3$
2-aminoethyl-aminopropyltriethoxysilane
$H_2N-(CH_2)_2-NH-(CH_2)_3-Si-(OC_2H_5)_3$
2-aminoethyl-aminopropylmethyldimethoxysilane

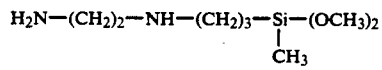

The synthesis reaction is conducted by gradually adding the isatoic anhydride to the aminosilane in the presence or absence of solvent.

If the reaction is carried out in solvent this must not react with the isatoic anhydride. In the case of hydroxyl solvents, mild reaction conditions must be used, for example, with no catalysts. Alcohols, ethers, chlorinated solvents etc. can be used as solvents. The process must be conducted in the absence of water, which would hydrolyze the alkoxy groups.

The reaction can also be effected by adding the isatoic anhydride in one addition taking account of the slight exothermic nature of the reaction (cooling is required) and the fact that in spite of the considerable reactivity difference between the aliphatic amine (aminosilane) and the aromatic amine (reaction product), oligomer products of the type

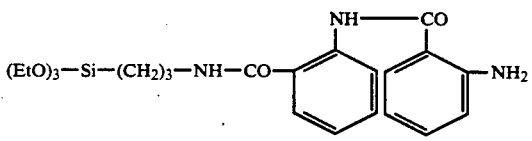

could form, even if only in minimum quantity. Enzyme types which produce electrical charges during the catalyzed reaction can be introduced into said device.

Any proteins used can be chosen for example from albumin, hemocyanin etc.

The said immunosensor can be used to determine, in biological fluids, particular circulating antibodies such as those directed against malaria plasmodium or the AIDS virus (HTLVIII), the detection of which is important in clinical diagnostics.

These antibodies are determined by putting them in competition with the free antigen or with analogous antibodies having the same specificity marked with an enzyme such as glucose oxidase, urease or others which during the catalyzed reaction produce eletrical charges detected by the transducer (EOS or FET).

An alternative measurement process is to use a second antibody directed towards the first, or protein A or protein G of microbic origin, marked with an enzyme such as glucose oxidase or urease or others having the aforesaid characteristics.

In addition, the immunosensor of the present invention can be used to determine contaminant substances such as atrazine herbicides, paraquat, molinate or others for which the relative functionalized antigen can be constructed.

Atrazine is a herbicide widely used in agriculture mainly for maize cultures, and acts by interfering with the photosynthesis system of the infesting plants.

The selectivity with respect to maize is due to the fact that the active principle is degraded by the culture by means of specific enzymes or polyphenols, into a nontoxic substance (hydroxyatrazine).

The use of this herbicide can cause pollution of waters surrounding the treated cultures, where it can remain for a long time before undergoing natural degradation.

The determination of atrazine in aqueous solutions is commonly effected by complex analytical processes such as gas chromatography (GC), HPLC (high performance liquid chromatography) or GLC after a preliminary purification procedure. The use of the immunosensor of the present invention would have the advantage over the aforesaid processes of being able to directly analyze the samples in aqueous solution.

In addition the construction of portable instruments would make it possible to directly analyze atrazine in the field.

To determine atrazine by the immunosensor according to the present invention, antibodies directed against this substance must be used.

As atrazine is a small molecule and in itself is not immunogenic (i.e. it does not cause antibody production) an atrazine analogue, namely ametryne, is used functionalized as ametryne sulphoxide (N-ethyl-N'-isopropyl-6-methylsulfoxide-1,3,5, -triazine-2,4-diamine) and bonded by this reactive group to a carrier (generally a protein such as albumin, hemocyanin or others).

This conjugate, once inoculated into a rabbit (or another suitable experimental animal) induces the production of antibodies which recognize both ametryne and atrazine itself.

Using an analogous system antibodies can be obtained against other contaminant substances such as paraquat, molinate etc., as described in the literature [e.g. J. Van Emon, B. Hammock. J. N. Seiber; Anal. Chem. (1986), 58, 1866–1873; S. J. Gee, T. Miyamoto, M. H. Goodrow, D. Buster, B. D. Hammock; J. Agric. Food Chem. (1988), 36, 863–870].

In constructing said immunosensor, either said ametryne-protein conjugate can be chemically bonded to the device by bifunctional coupling reactants, or ametryne sulphoxide can be directly bonded thereto by said reactive group.

This second process in which the ametryne is directly bonded without forming a protein membrane results in increased resistance of the membrane.

The present invention also provides processes which can be used to form the device with an immunochemical membrane.

A first process for constructing the sensor with the immunochemical membrane formed from a monolayer consisting of a functionalized antigen comprises the following steps:
- preparing a siloxane prepolymer followed by one or more depositions thereof on an EOS or CHEMFET device and thermal curing by which complete polymerization of the silane alkoxy groups takes place by hydrolysis to obtain a polysiloxane matrix and consequent chemical adhesion of said matrix to the silicon oxide by reaction of other alkoxy groups with the Si-OH hydroxyls present on the oxidized surface;
- reacting the previously functionalized antigen with the aliphatic amino groups present on the polysiloxane layer.

A second process for constructing the sensor with the immunochemical membrane formed from a polymer multilayer consisting of a functionalized antigen and a protein comprises the following steps:
- preparing a siloxane prepolymer followed by one or more depositions thereof on an EOS or CHEMFET device and thermal curing by which complete polymerization of the silane alkoxy groups takes place by hydrolysis to obtain a polysiloxane matrix and consequent chemical adhesion of said matrix to the silicon oxide by reaction of other alkoxy groups with the Si—OH hydroxyls present on the oxidized surface;
- activating the aliphatic amino groups present on the polysiloxane layer by bifunctional coupling agents;
- preparing an immunochemical prepolymer consisting of the functionalized antigen bonded to a protein;
- reacting the immunochemical prepolymer with the activated amino groups of the polysiloxane layer.

The bifunctional coupling agents used in the aforesaid process can be chosen from dialdehydes (such as glutaraldehyde) or from diisocyanates (such as toluene 2.4-diisocyanate).

Deposition of the siloxane prepolymer in the aforesaid processes can be accomplished by spin-on techniques, and the polysiloxane layer can be activated and reacted with the antigen and protein on a rocking plate.

The thermal curing of the siloxane prepolymer is effected at a temperature of between 80° and 140° C., the subsequent immunochemical immobilization treatment being between 25° and 37° C.

The thickness of the deposited siloxane prepolymer must be between 0.5 and 3μ, and the thickness of the immunochemical membrane can be between 0.5 and 2μ.

To form the polysiloxane layer the rotary disc apparatus must operate at a speed preferably of between 400 and 4500 rpm during the depositions.

The siloxane prepolymer can also be deposited on silicon or silicon oxide substrates of EOS or ISFET devices by plasma deposition, preferably under the following conditions:
- power between 20 and 50 W;
- discharge pressure between 0.1 and 1 torr;
- temperature between ambient and the decomposition temperature of the siloxane prepolymer used.

In the particular case of a sensor for determining atrazine the preferred silanes are AEAPS and 3-APTS.

The present invention also provides a process for measuring the unknown antigen concentration using the EOS or CHEMFET electronic devices as transducers.

Determination of the antigen concentration is accomplished by marking the antibody directed against the antigen itself, or marking a second antibody directed against the antigen-recognizing antibody, with an enzyme such as glucose oxidase, urease or others, which during the catalyzed reaction produces electrical charges detected by the transducer (EOS or FET).

In the first case the antibody-enzyme conjugate is made to compete with the antigen to be determined. The quantity of marked antibody bonded to the immunochemical membrane present on the device can be determined by the electrical response of the enzyme in the presence of its substrate. This quantity is therefore inversely proportional to the quantity of antigen present in solution to be determined.

In contrast, in the second case after the antibody has been bonded to the antigen immobilized on the device a second antibody marked with the enzyme directed against the first antibody is added. Thus the concentration of the antigen to be determined is again inversely proportional to the quantity of marked antibody bonded to the first antibody, determined on the basis of the enzyme electrical response recorded by the transducer.

This process has therefore the advantage of less interference due to ions or to other proteins present in the sample under examination, as the measurment is obtained by the electrical response of the enzyme, which marks an antibody directed against the antigen or a second antibody directed against the first antibody, when in the presence of its substrate.

Examples are given below to better illustrate the invention, but without limiting it.

EXAMPLE 1

Preparation of ametryne-EOS

Ametryne sulphoxide is prepared from commercial ametryne as reported by Huber S. J. (1985) in Chemosphere vol. 14 No. 11/12, pp. 1795-1803.

The formation of the ametryne sulphoxide is monitored by ETIR (Fourier transform infrared spectroscopy), as shown in FIG. 1, the sulphoxide showing strong absorption at 1035 cm$^{-1}$.

(The horizontal axis represents wavelength in cm$^{-1}$ and the vertical axis represents percentage transmittance).

An immunosensor was formed enabling an immunochemical membrane to be obtained from a monolayer consisting of a functionalized antigen (ametryne sulphoxide) bonded chemically to the polysilozane matrix.

A solution of partially hydrolyzed polsiloxane in a hydroalcoholic environment containing:
21% of amino-ethylaminopropyltrimethoxysilane (AEAPS)
3% of acetic acid
1% of $H_2O$
in absolute ethanol was deposited on 0.5 cm×0.5 cm bars of an EOS device.

Three depositions were effected by a rotary disc apparatus rotating at 3500 rpm for 20 seconds.

Any excess of this oligomer solution deposited on the EOS was removed by centrifugal action deriving from the rotary movement of the carrying plate. After thermal curing for 16 hours at 120° C. the bars were cooled. Each bar was placed in a weighing filter in 1 ml of a solution of 0.5 mg of ametryne sulphoxide in pH 9.6 50 mM carbonate buffer containing 10% of absolute ethanol and agitated on a rocking plate for 5 days at ambient temperature, then washed three times with pH 7.8 50 mM TRIS buffer containing 10% of absolute ethanol and a further two times with the same buffer but without the ethanol.

Conjugation protein-ametryne sulphoxide

200 μl of absolute ethanol containing 12 mg of ametryne sulphoxide were added to 50 mg of bovine serum albumin (BSA) dissolved in 5 ml of 9.6 pH 50 mM carbonate buffer.

The mixture was incubated for 5 days in the dark at 37° C., dialyzed against 5 liters of 0.9% NaCl and lyophilized. The lyophilized product was used to produce antibodies as shown in Table 1.

Figure 2:
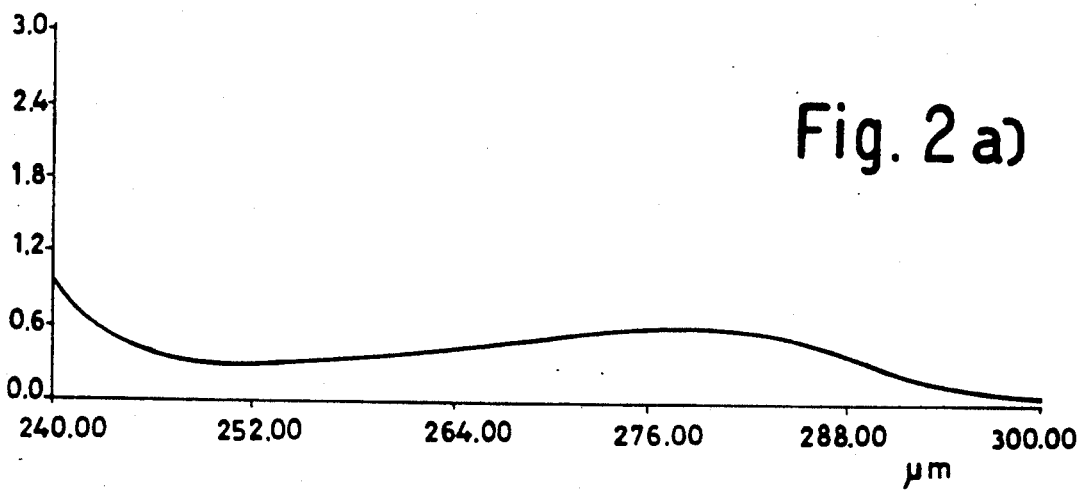
FIG. 2a is showing the absorption spectra of BSA.
FIG. 2b is showing the absorption spectra of commercial ametryne.
FIG. 2c is showing the absorption spectra of BSA-ametryne.
Figure 2:
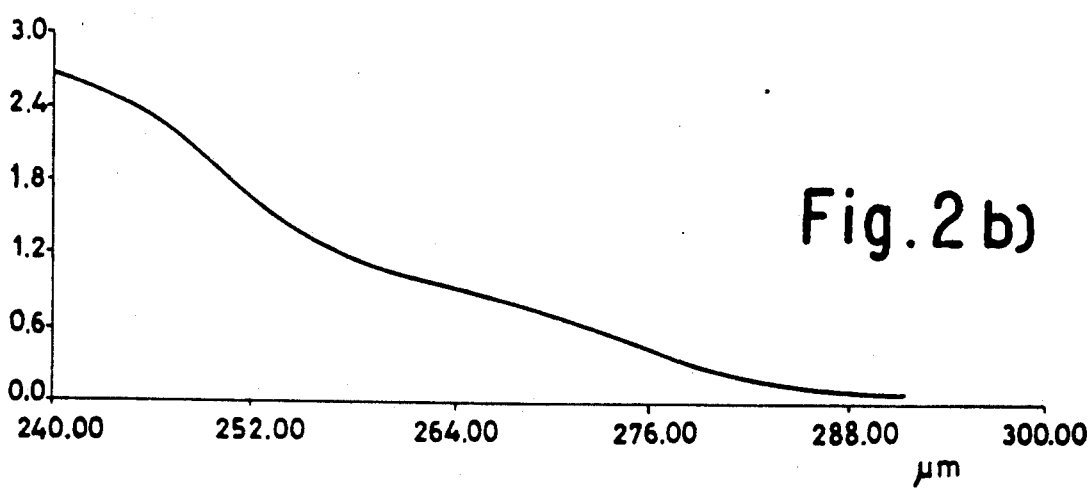
Figure 2:
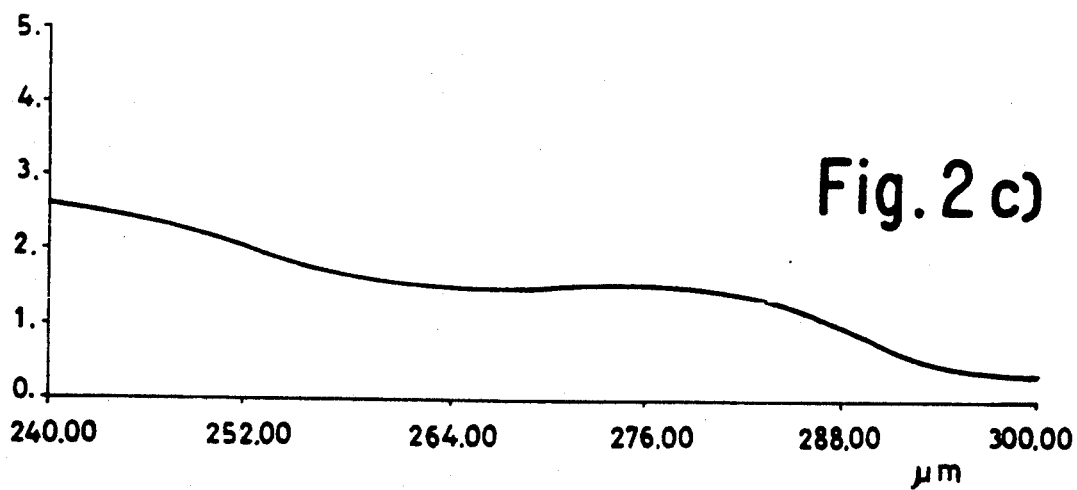

FIG. 2 shows the absorption spectra of BSA (a), commercial ametryne (b) and the compound BSA-ametryne (c). (The horizontal axis represents wavelength in μm and the vertical axis the optical density).

A like procedure was carried out to conjugate Helix pomatia hemocyanin with ametryne sulphoxide.

Coating ametryne on the plate

100 μl of a solution of BSA-ametryne (300 μg/ml in pH 7.8 50 mM TBS) were incubated in each of various wells in a plate overnight at ambient temperature (Nunc Immunoplate Maxisorpt F 96).

100 μl of a solution of BSA (300 μg/ml in pH 7.8 50 mM TBS) were incubated in certain wells in the same plate overnight at ambient temperature.

100 μl per well of a solution of hemocyanin-ametryne (300 μg/ml in pH 7.8 50 mM TBS) were incubated in certain other wells in the same plate overnight at ambient temperature.

100 μl of a solution of hemocyanin (300 μg/ml in pH 7.8 50 mM TBS) were incubated in certain other wells in the same plate overnight at ambient temperature.

The plate was then washed 5 times with 200 μl per well of pH 7.8 25 mM TBS containing 0.05% of Tween 20.

200 μl of pH 7.8 50 mM TBS containing 5% BSA were incubated in each well for 1 hour at ambient temperature.

The plate was then washed 5 times with 200 μl per well of pH 7.8 25 mM TBS (+0.05% of Tween 20).

Titration of the antiserum by ELISA

100 μl per well of immune serum or non-immune serum diluted to between 1:500 and 1:32000 in pH 7.8 25 mM TBS (+2.5% BSA +0.05% Tween 20) were then incubated in the same plate for 1 hour at ambient temperature.

The plate was then washed 5 times with 200 μl per well of pH 7.8 25 mM TBS (+0.05% of Tween 20).

Incubation was then carried out with 100 μl of Goat-Anti-Rabbit IgG-HRP (1:4000) in pH 7.8 25 mM TBS (+2.5% BSA +0.05% Tween 20) for 1 hour at ambient temperature.

The plate was then washed 5 times with 200 μl per well of pH 7.8 25 mM TBS (+0.05% of Tween 20).

Incubation was then carried out with 100 μl of substrate (TMB) (3,3',5,5'-tetramethylbenzidine) at ambient temperature and the reaction blocked after 5 minutes with 100 μl of 0.5M sulphuric acid. The absorbance at 450 nm was read against blank-substrate blocked with sulphuric acid.

The substrate (TMB) consisted of:
9 ml of pH 5.0 0.1M acetate buffer and 1 ml of a 3,3',5,5'-tetramethylbenzidine solution (1 mg/ml in 0.1M citric acid + 1.5 μl of 35% hydrogen peroxide).

Figure 3:
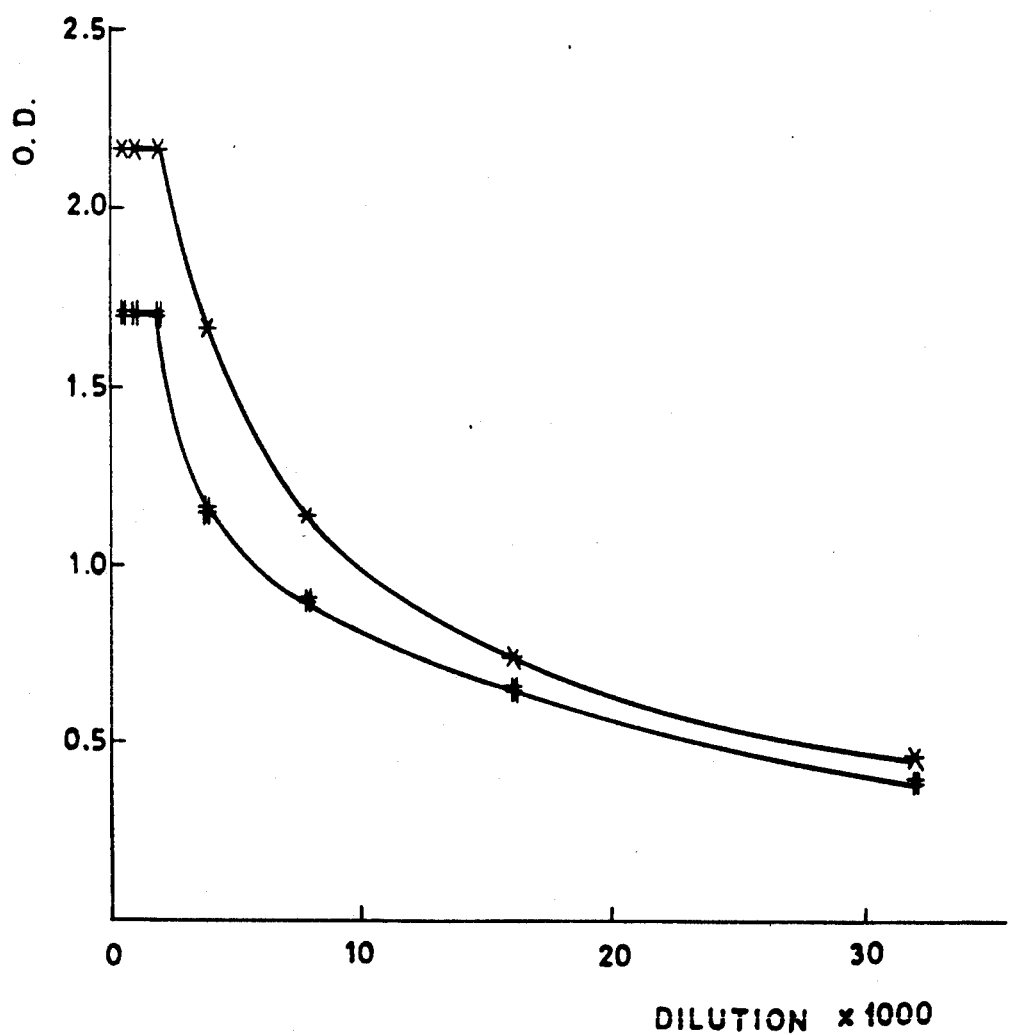
FIG. 3 is showing curves representing titration of anti-ametryne antiserum with BSA-ametryne and hemocyanin-ametryne in a plate.

FIG. 3 shows the curves representing titration of anti-ametryne antiserum with BSA-ametryne (*) and hemocyanin-ametryne (#) supported in the plate. (The horizontal axis represents dilution × $10^3$ and the vertical axis represents optical density.)

The EOS-ametryne and other EOS (AEAPS) samples used as blanks were incubated with 0.5 ml of immune serum diluted to between 1:500 and 1:4000 in pH 7.8 50 mM TBS (+0.5% casein +0.1% Triton X100 +2% PEG 6000) for 30 minutes at ambient temperature.

Washing was then carried out 4 times with 1 ml of pH 7.8 50 mM TBS (+0.1% Triton X100), using 5 minutes residence time.

Incubation was then carried out with 0,5 ml of Goat-Anti-Rabbit IgG-HRP (1:4000) in pH 7.8 50 mM TBS (+0.5% casein +0.1% Triton X100 +2% PEG 6000) for 30 minutes at ambient temperature.

Washing was then carried out 4 times with 1 ml of pH 7.8 50 mM TBS (+0.1% Triton X100), using 5 minutes residence time.

Incubation was then carried out with 0.5 ml of substrate (TMB) at ambient temperature and the reaction blocked after 10 minutes with 0.5 ml of 0.5M sulphuric acid.

Figure 4:
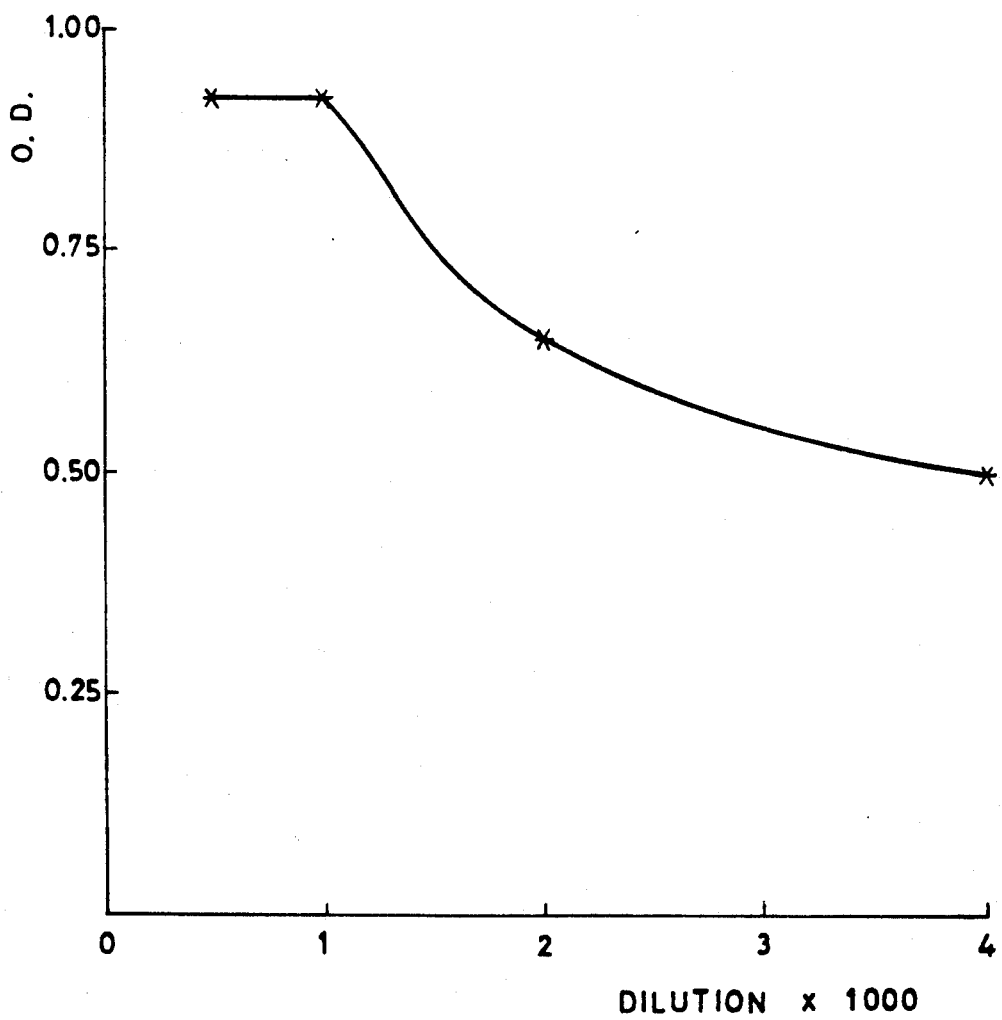
FIG. 4 is showing the curve representing titration of anti-ametryne antibodies with Eos ametryne samples.

200 μl were transferred into a well of an ELISA plate and the absorbance was read at 450 nm against blank-substrate. The titration curve is shown in FIG. 4 (in which the horizontal axis represents dilution × $10^3$ and the vertical axis represents optical density.)

Determination of inhibition with various atrazine concentrations

EOS (AEAPS) and EOS-ametryne were incubated with 0.5 ml of immune serum diluted to 1:2000+atrazine (0.05, 1, 5 and 25 μg/l) in pH 7.8 50 mM TBS (+0.5% casein +0.1% Triton X100 +2% PEG 6000) for 30 minutes at ambient temperature.

Washing was then carried out 4 times with 1 ml of pH 7.8 50 mM TBS (+0.1% Triton X100), using 5 minutes residence time.

Incubation was then carried out with 0.5 ml of Goat-Anti-Rabbit IgG-HRP (1:4000) in pH 7.8 50 mM TBS (+0.5% casein+0.1% Triton X100+2% PEG 6000) for 30 minutes at ambient temperature. Washing was then carried out 4 times with 1 ml of pH 7.8 50 mM TBS (+0.1% Triton X100), using 5 minutes residence time.

Incubation was then carried out with 0.5 ml of substrate (TMB) and the reaction blocked after 10 minutes with 0.5 ml of 0.5M sulphuric acid.

200 μl of each mixture were transferred into a well of an ELISA plate and the absorbance was read at 450 nm against blanksubstrate.

Figure 5:
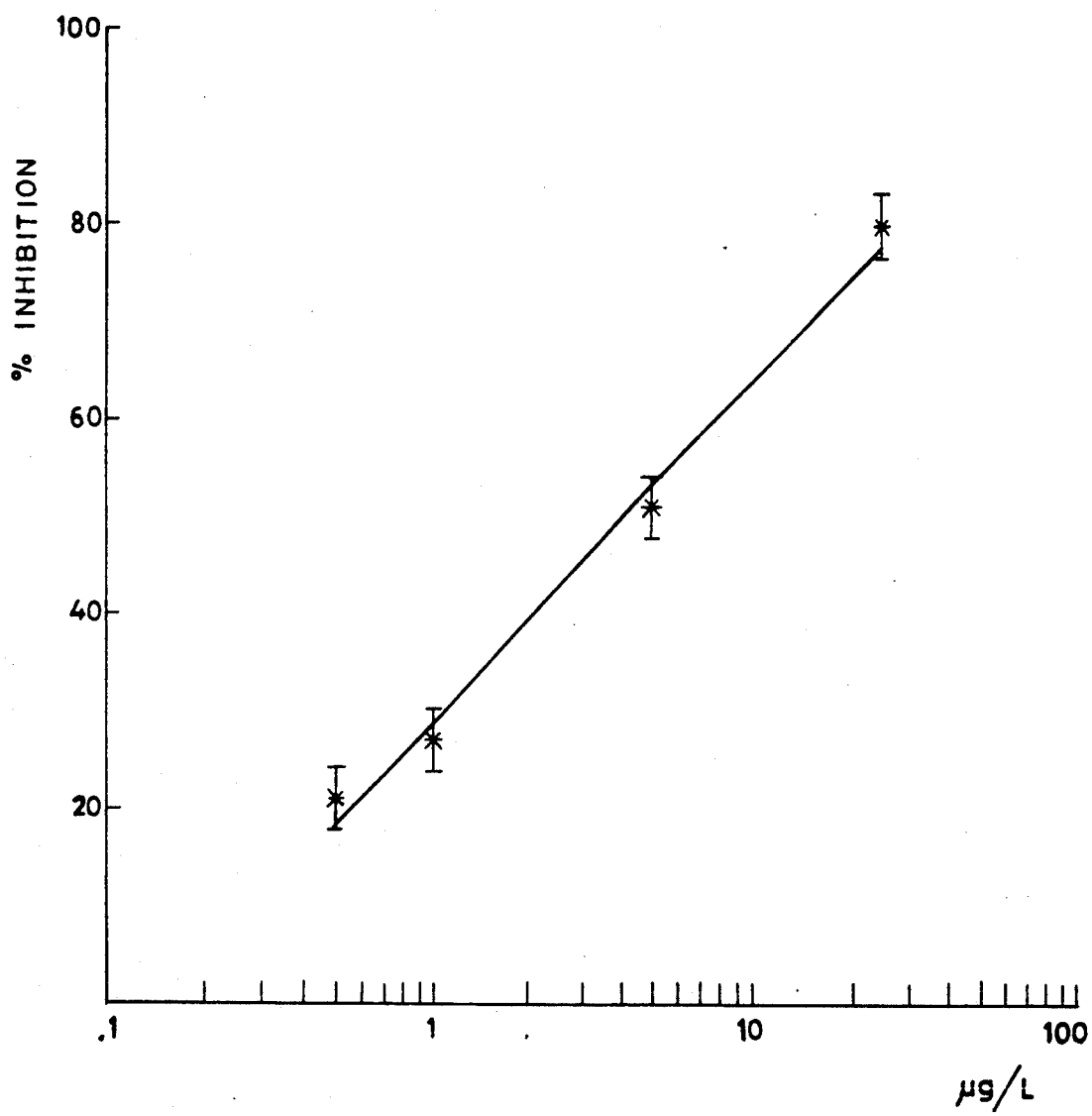
FIG. 5 is showing the percentage inhibition with respect to the atrazine concentration.

The percentage inhibitions are given in FIG. 5 (in which the horizontal axis represents the atrazine concentration in μg/l).

EXAMPLE 2

Immobilization of ametryne on FET devices

The chip (HEDCO, University of Utah), having a size of 1.28 mm×2.16 mm and comprising two 400 μm×20 μm gates, stuck onto a slide by adhesive tape (3M electrical tape 92) to protect the electrical contact region and edges but leaving the gates free.

A layer of AEAPS [3(2-aminoethyl)aminopropyl-trimethoxysilane] was then deposited on it as described heretofore. After depositing the polysiloxane, the chip was mounted on a type TO-5 support, contacted with an ultrasonic welder (Kulicke and Soffa mod. 4123) and then encapsulated with Epotek H-77 epoxy resin.

Some FET devices were reacted for 5 days at ambient temperature under agitation, each with 0.5 ml of a solution of about 1 mg/ml of ametryne sulphoxide in 50 mM pH 9.6 carbonate buffer, containing 10% of absolute ethanol. They were then washed three times with 50 mM pH 7.8 TBS buffer containing 10% of ethanol and then twice with the same buffer without ethanol.

The devices were incubated with 0.5 ml of immune serum diluted 1:500 in 50 mM pH 7.8 TBS buffer containing 2.5% BSA, 0.1% Triton X-100 and 2% PEG 6000 (Incubation Buffer), for 30 minutes at ambient temperature.

They were washed 4 times (5 minutes residence) with 0.5 ml of 50 mM pH 7.8 TBS containing 0.1% Triton X-100 (Wash Buffer). They were incubated with 0.5 ml of a solution of Goat-Anti-Rabbit IgG-GOD in Incubation Buffer for 30 minutes at ambient temperature.

They were washed 4 times with the Wash Buffer. The electrical response produced by the activity of the GOD in the presence of glucose was then measured.

Figure 6:
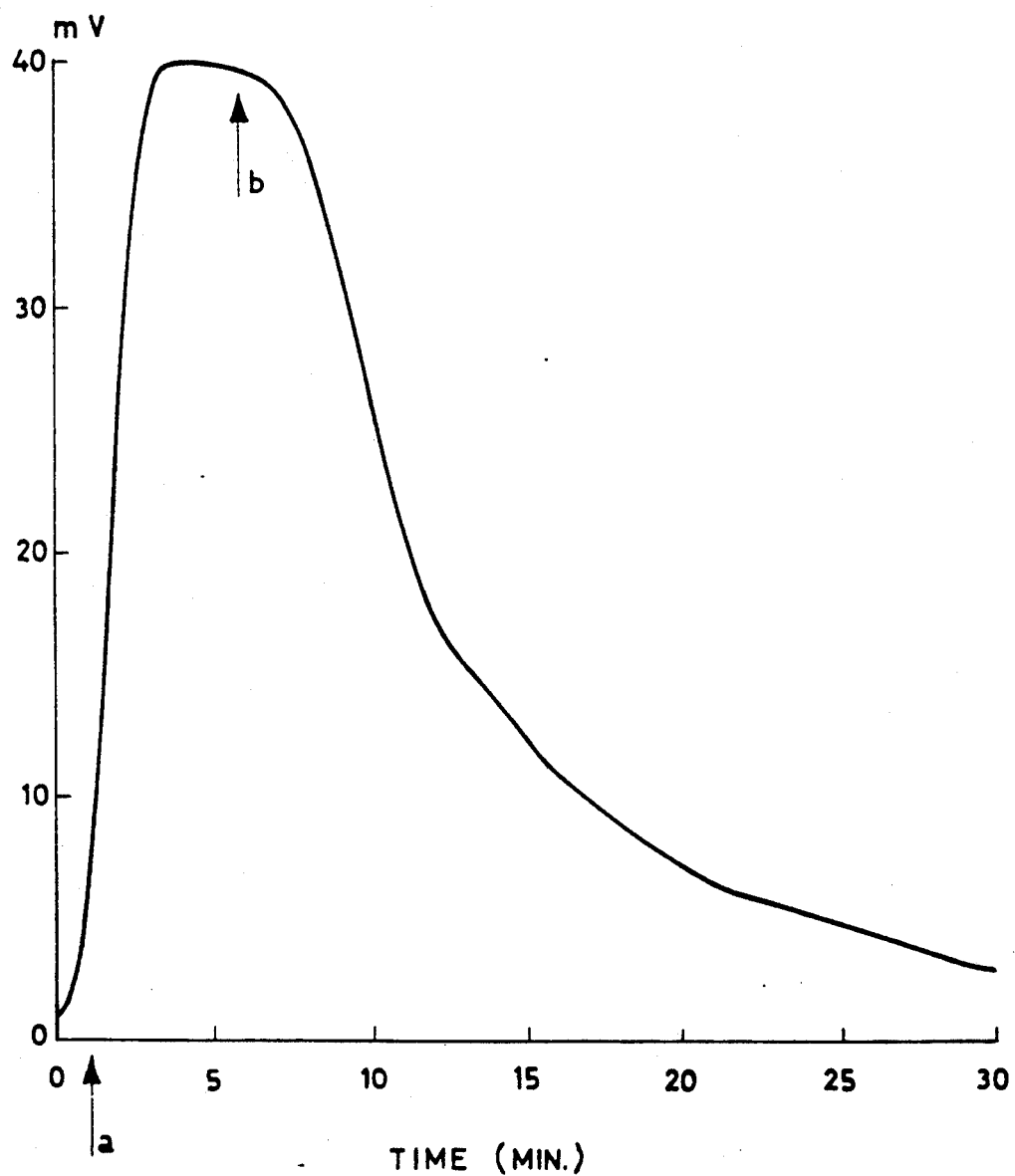
FIG. 6 shows the curve of immunosensor electrical response after addition of glucose (at time a) and after the addition of the wash buffer and phosphate (at time b).

FIG. 6 shows the curve of immunosensor electrical response after the addition of 0.05M glucose (at time a) and after the addition of the Wash Buffer and 20 mM pH 7.0 phosphate (at time b). The horizontal axis represents time in minutes and the vertical axis represents the electrical response in mV.

EXAMPLE 3

Reversibility of the immunofet

Some FETs were reacted for 1 hour at ambient temperature under agitation with 0.250 ml of a 10 mg/ml solution of BSA-ametryne in 20 mM pH 7.0 phosphate buffer, in the presence of 0.1% glutaraldehyde, and were then washed with only buffer.

They were incubated for 30 minutes at ambient temperature with 0.5 ml of immune serum diluted 1:500 in Incubation Buffer, and washed 4 times with the Wash Buffer.

They were then incubated with 0.5 ml of a solution of Goat-Anti-Rabbit IgG-GOD in Incubation Buffer for 30 minutes at ambient temperature.

They were washed 4 times with the Wash Buffer. The electrical response produced by the activity of the GOD in the presence of glucose was then measured.

After the electrical measurement the chip was incubated for about 10 minutes with 0.1M pH 2.0 glycine-HCl buffer to obtain antigenantibody separation, so regenerating the device to allow it to be used for a further measurement.

It was re-incubated with immune serum and Goat-Anti-Rabbit IgG-GOD as described above, and the electrical response was measured.

Figure 7:
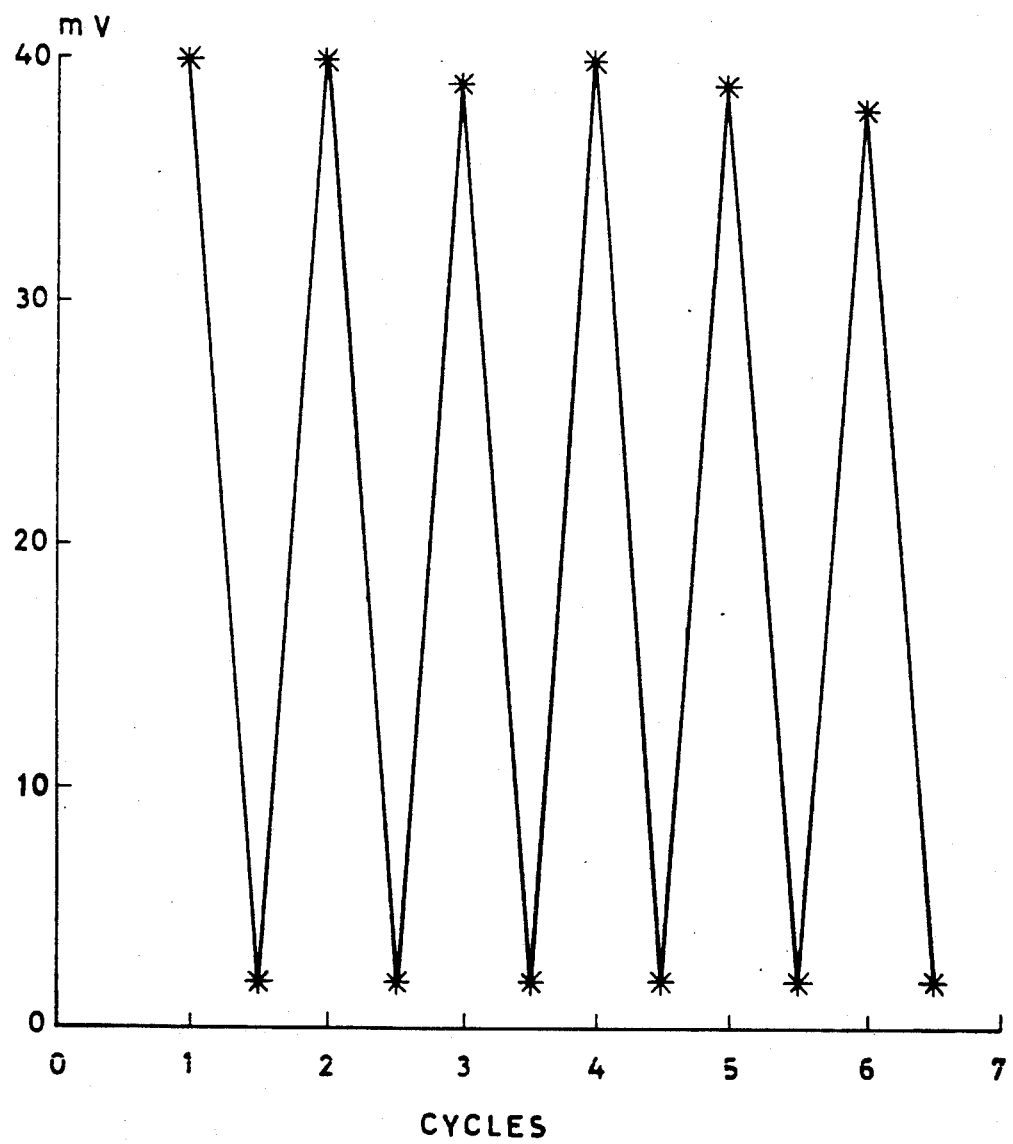
FIG. 7 shows the response obtained during various cycle effected with the same device.

FIG. 7 shows the response in mV (vertical axis) obtained during various cycles effected with the same device.

Determination of inhibition in the presence of atrazine

The FET-BSA-ametryne was incubated with 0.5 ml of immune serum diluted 1:500 in Incubation Buffer for 30 minutes at ambient temperature, and washed 4 times with the Wash Buffer.

It was then incubated with 0.5 ml of a solution of Goat-Anti-Rabbit IgG-GOD in Incubation Buffer for 30 minutes at ambient temperature.

It was washed 4 times with the Wash Buffer.

The electrical measurement in the presence of glucose was then made. After this measurement had been made in the absence of atrazine, regeneration, i.e. the separation of the antigen from the antibody, was effected using 0.1M pH 2.0 glycine-HCl buffer.

The incubation was repeated as described above after adding quantities of atrazine equivalent to 1 to 5 ppb to the antiserum, and the electrical response was recorded.

Figure 8:
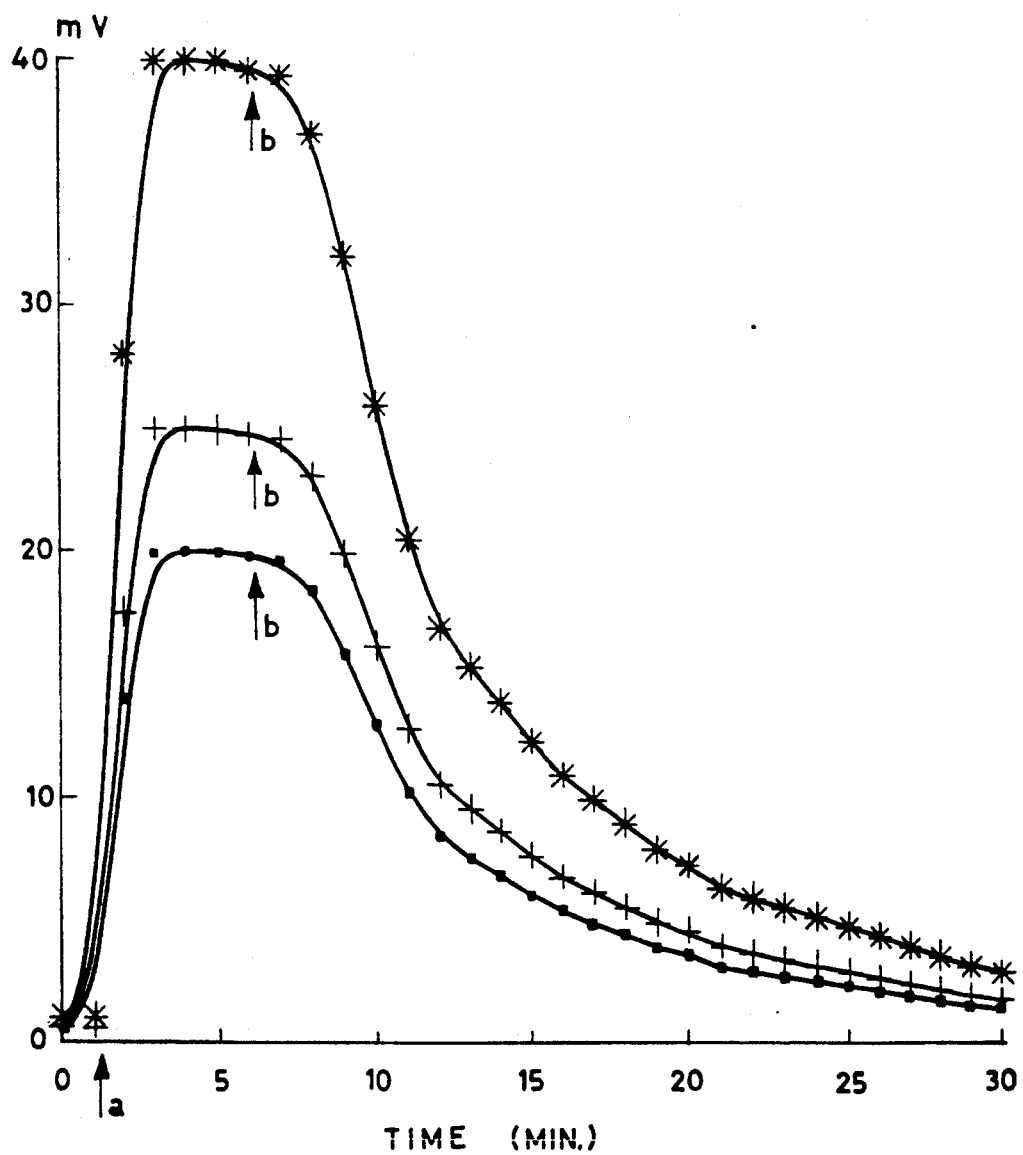
FIG. 8 shows the electrical response curves after adding glucose (at time a) and the after adding wash buffer and phosphate (at time b) in the presence atrazine at difference concentration levels.

FIG. 8 shows the electrical response curves, namely: after adding 0.05M glucose (at time a); after adding the Wash Buffer and 20 mM pH 7.0 phosphate (at time b); in the presence of 0 ppb (*), 1 ppb (+) and 5 ppb (=) of atrazine (the horizontal axis represents time in minutes, and the vertical axis represents electrical response in mV).

TABLE 1

| RABBIT IMMUNIZATION WITH BSA-Ametryne | | |
| --- | --- | --- |
| Day | Conjugate | Application |
| 1 | 1 mg in 0.5 ml of 0.9% NaCl +0.5 ml of complete Freund's adjuvant | endodermic |
| 11 | as above | endodermic |
| 19 | as above | endodermic |
| 27 | 1 mg in 0.5 ml of 0.9% NaCl | intravenous |
| 41 | Blood sample taken | |
| 88 | 1 mg in 0.5 ml of 0.9% NaCl | intravenous |
| 102 | Blood sample taken | |

We claim:
1. A sensor constructed of an imunochemical membrane adhering to a silicon oxide surface of an electrolyte oxide semiconductor or a chemical field effect transistor through a polysiloxane matrix, said imunochemical membrane formed from a monolayer consisting of a functionalized antigen or a polymeric multilayer consisting of a functionalized antigen and a protein, said imunochemical membrane being directly bonded chemically to the polysiloxane matrix by functional groups present on the said antigen or by bifunctional coupling agents present on said protein and the polysiloxane matrix being chosen from organosilanes of the formula:

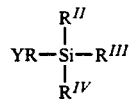

wherein $R^{II}$, $R^{III}$ and $R^{IV}$, which may be the same or different, are each $C_{1-10}$ alkyl or alkoxy, R is $(CH_2)_mX(CH_2)_n$, wherein X is $CH_2$ or a mono- or poly-condensed aromatic group, NH or O; m and n, which are equal or different, are each 0–10, but not 0 when X is NH or O; Y is $-NH_2$, $-OH$ or $-SH$; or from functional organosilanes of the formula:

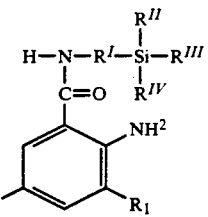

wherein $R_1$ and $R_2$, which are the same or different, are Cl, Br, $CH_3$, $NO_2$, $NH_2$ or H; $R^{II}$, $R^{III}$ and $R^{IV}$, which are the same or different, are $C_{1-10}$ alkyl or alkoxy groups and $R^I$ is $C_{1-10}$ alkyl, aminoalkyl, aminoalkylaryl or alkylaryl.

2. The sensor as claimed in claim 1, wherein the functionalized antigen is N-ethyl-N'-isopropyl-6-methylsulfoxide-1,3,5-triazine-2,4-diamine.

* * * * *